United States Patent

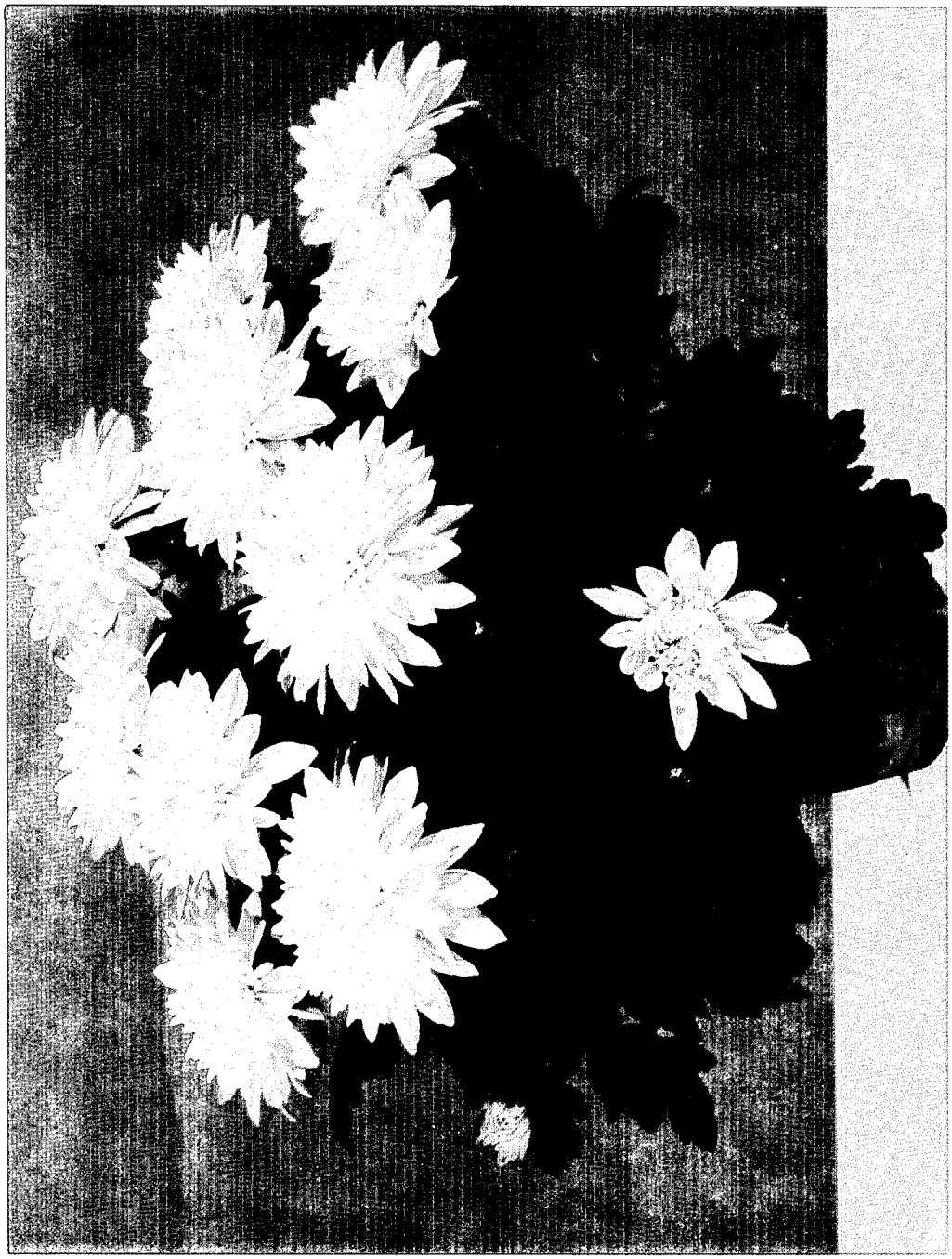

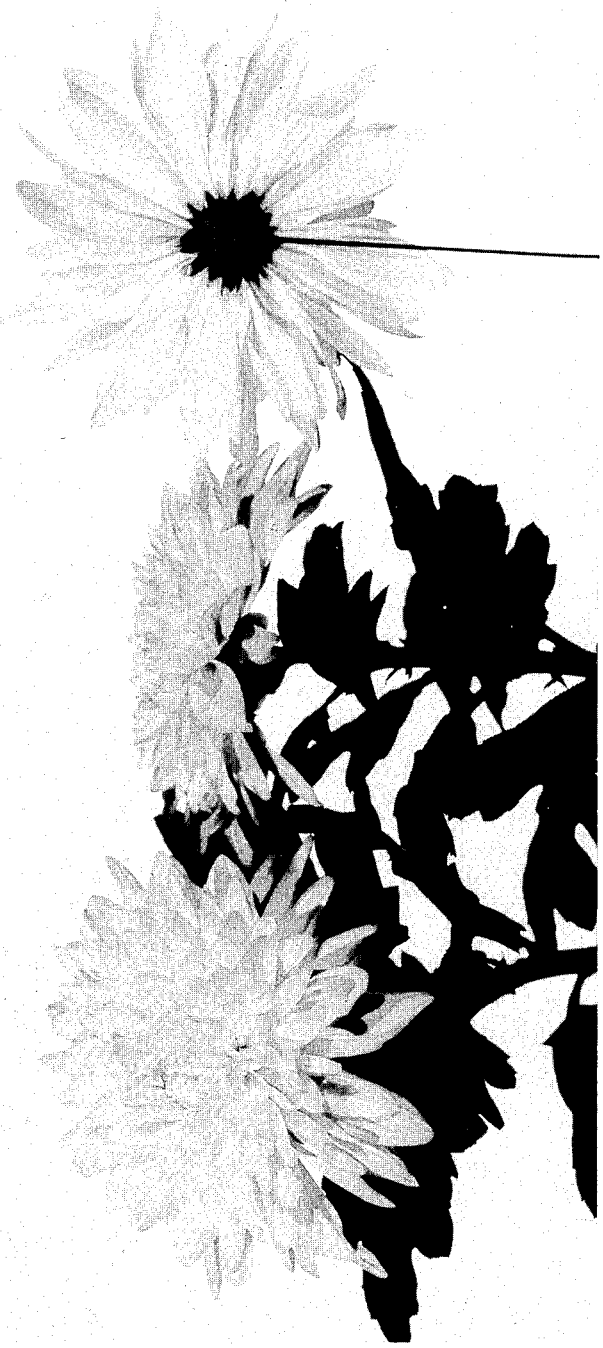

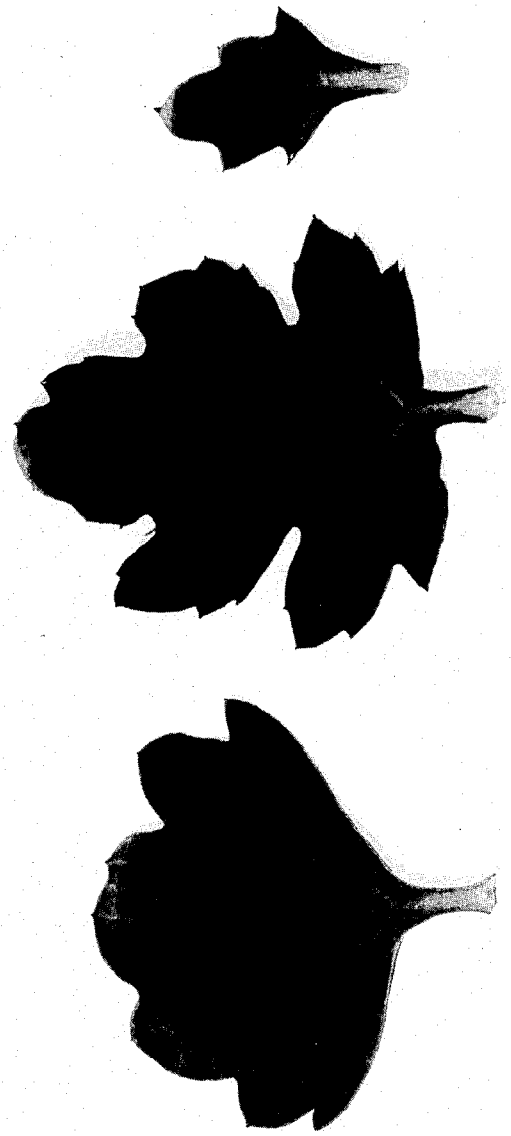

Plant Pat. 3,867

Patented Apr. 20, 1976

3,867

CHRYSANTHEMUM PLANT

Walter H. Jessel, Jr., Doylestown, and William E. Duffett, Akron, Ohio, assignors to Yoder Brothers, Inc., Barberton, Ohio Filed Jan. 17, 1975, Ser. No. 541,952

Int. Cl. A01h 5/00

U.S. Cl. Plt.—78 1 Claim

The present invention comprises a new and distinct cultivar of *Chrysanthemum morifolium,* hereinafter referred to by the cultivar name Tip (#71328013).

Tip was originated from a cross made in a controlled breeding program in Barberton, Ohio in the year 1970.

The male, or pollen parent, was #70031002 (unnamed seedling), a decorative of cream yellow color originated by the present inventors from a cross between Sunstar (#61525010; unpatented; commercially available) and Mandalay (#61865001; unpatented; commercially available). Both parents were products of the breeding program of the present inventors.

The female, or seed parent, was #70048004 (unnamed seedling), a decorative of yellow color originated by the present inventors from a cross between Sunstar (#61525010; unpatented; commercially available) and Mandalay (#61865001; unpatented; commercially available). Both patrents were products of the breeding program of the present inventors.

Tip was discovered and selected as a flowering seedling within the progeny of the stated cross by William E. Duffet and Walter H. Jessel, Jr. on Dec. 10, 1971 in a controlled environment in Barberton, Ohio.

Tip is a product of a planned breeding program which had the objective of creating a durable yellow decorative adaptable to pot chrysanthemum culture that would fulfill in part or in whole the need for a golden yellow decorative chrysanthemum with efficient crop time and fast response during high light and high temperature periods when grown as a pinched disbudded pot plant.

The first act of asexual reproduction of Tip was accomplished when vegetative cuttings were taken from the initial selection in April 1972 in a controlled environment in Barberton, Ohio by technician according to formulations established and supervised by William E. Duffet and Walter H. Jessel, Jr.

Continued asexual reproduction by vegetative cuttings for evaluative tests in flowering and stock programs in conjunction with horticultural certification initiated Aug. 1, 1973 have demonstrated that the combination of characteristics are herein disclosed for Tip are firmly fixed and are retained through successive generations of asexual reproduction.

The following descriptive observations, measurements, and comparisons were derived from plants grown as a pinched, disbudded pot in a greenhouse in Barberton, Ohio under conditions which closely approximate those generally used in commercial practice (as described in Chart A and Chart B which are attached at the end of the specification).

The following traits have been repeatedly observed and are determined to be basic characteristics of Tip which in combination distinguish this chrysanthemum as a new and distinct cultivar.

(1) Decorative type inflorescence of informal form.

(2) Diameter of face of inflorescence up to 5½ inches at maturity.

(3) Golden yellow ray floret color devoid of bronze tinging and with minimal color oxidation.

(4) Flowering response is uniform and consistent, resulting in a flowered plant approximately 8 weeks from the beginning of short day treatment (under environmental conditions as defined in Chart A and Chart B).

(5) Growth habit is strong and semi-spreading.

(6) Height is responsive to daylength control and B–9 for adaptability to various pot sizes.

(7) Foliage is dark green and glossy.

(8) Durability of the flowered plant ranges up to 21 days at average home temperatures of 68° F. to 75° F.

(9) Peduncles become brittle and weak during low light periods of the year (November thru April).

The accompanying photographic drawings show typical inflorescence and foliage characteristics of Tip, with the colors being as nearly true as possible with illustrations of this type. Sheet 1 comprises a color photograph of Tip. Sheet 2 is a black and white photograph showing three different views of the inflorescence of Tip. Sheet 3 is a black and white photograph showing the foliage of Tip at various stages of growth.

The phenotype of Tip may vary significantly with variations in environment such as temperature, light intensity, and daylength outside the ranges defined in Chart A and Chart B. The genotype of Tip was not observed under all possible environments.

Known commercially available cultivars with which Tip may appropriately be compared are Bright Golden Anne (unpatented), Goldstar (U.S. Plant Pat. #3,213), Sunny Mandalay (U.S. Plant Pat. #3,231), and Wild Honey (U.S. Plant Pat. #3,359). Reference is made to attached Chart C which compares certain characteristics of the above mentioned varieties with the same characteristics of Tip. General comparisons are as follows:

(1) In comparison to Bright Golden Anne, Tip has shorter response period, more spreading growth habit, and less formal inflorescence form. The ray floret color, inflorescence type, height, and diameter across the face of inflorescence of Tip are the same as those of Bright Golden Anne.

(2) In comparison to Goldstar, Tip has more intense ray floret color, shorter response period, taller height, and larger diameter across the face of inflorescence. The spreading growth habit and the inflorescence form and type of Tip are the same as those of Goldstar.

(3) In comparison to Sunny Mandalay, Tip has shorter response period, less incurved (more informal) inflorescence form, taller height, and larger diameter across the face of inflorescence. The ray floret color, spreading growth habit, and inflorescence type of Tip are the same as those of Sunny Mandalay.

shatter. Color: Base: 23–3. Abaxial: 26–5 to 26–6. Adaxial: 23–3.

*C. Reproductive Organs.*—Androecium: present disc florets only. Stamen: syngenesious; 5 in number. Pollen: scant. Gynoecium: Ovary: inferior; bicarpellate. Style: single. Stigma: 2-lobed.

II. Plant:

*A. Habit.*—General appearance: semi-spreading; tall. Duration and texture: perennial; herbaceous.

*B. Foliage.*—Color: abaxial: between 20–15 and 20–13 with more grey. Adaxial: 19–13 overlaid with white. Shape: spatulate; slightly lobed. Textured: glabrous. Arrangement: alternate. Veination: prominent. Margin: moderately serrated.

CHART A.—AVERAGE GREENHOUSE CHRYSANTHEMUM ENVIRONMENTS USED FOR BARBERTON, OHIO

| Season | Temperatures used, °F. Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: On, 5:30 p.m.—Off, 7:30 a.m. | From Oct. 15, 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: On, 5:30 p.m.—Off, 7:30 a.m. | To Apr. 15, 300 p.p.m. |
| Summer | 62 to 68 | 70 to 90 | 65 to 75 | 1 to 2 weeks at 3 hours per night of 7–10 f.c. | On, 6:00 p.m.—Off, 8:00 a.m. | None. |

NOTE.—For intensity of direct solar radiation, refer to Chart B.

(4) In comparison to Wild Honey, Tip has shorter response period, more spreading growth habit, less incurved (more informal) inflorescence form, and smaller diameter across the face of inflorescence. The ray floret color of Tip is the same as that of Wild Honey under finishing night temperatures 60° F. and above (below 60° F. night finishing temperatures, Wild Honey develops bronzy overtones; Tip does not). The height of Tip is the same as that of Wild Honey.

In the following description, color references are to The Munsell Color Cascade, 1972 edition. The color values were determined between 8:00 a.m. and 8:30 a.m. on Sept. 16, 1974 under 30 foot candle light intensity at Barberton, Ohio.

Bontanical classification: *Chrysanthemum morifolium,* Ramat., cv Tip

I. Inflorescence:

*A. Capitulum.*— Form: informal. Type: decorative. Permanence: 18–21 days. Diameter across face: 4.75 inches to 5.5 inches.

*B. Corolla of ray florets.*—Texture (adaxial): glabrous. Appearance and form: ligulate. Arrangement: whorled in receptacle. Persistence: resists

CHART B

INTENSITY OF DIRECT SOLAR RADIATION

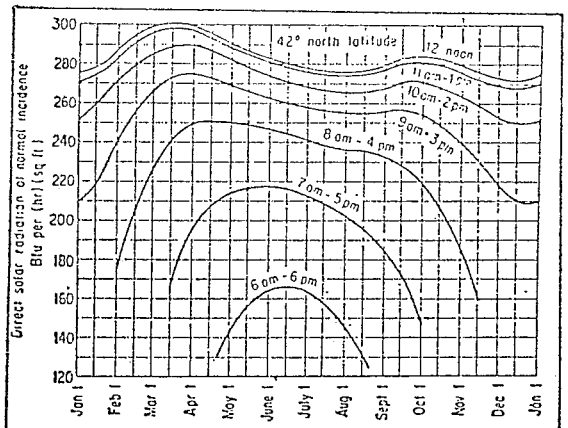

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C.—COMPARISON OF TIP WITH BRIGHT GOLDEN ANNE, GOLDSTAR, SUNNY MANDALAY AND WILD HONEY

| Cultivar | Ray floret color | Response period, weeks | Growth-habit | Inflorescence form and type | Height | Diameter across face of inflorescence, inches |
|---|---|---|---|---|---|---|
| Tip | Golden yellow | 8 | Semi-spreading | Informal decorative | Tall | 4¾–5½ |
| Bright Golden Anne | do | 10 | Semi-upright | Formal decorative | do | 4¾–5½ |
| Goldstar | Dark yellow | 9 | Semi-spreading | Informal decorative | Medium | 3¾–4¾ |
| Sunny Mandalay | Golden yellow | 10 | do | Semi-incurve decorative | Short | 3½–4 |
| Wild Honey | do | 9 | Semi-upright | do | Tall | 5¼–5¾ |

We claim:

1. A new and distinct cultivator of chrysanthemum characterized particularly by the combination of decorative type inflorescence of informal form; diameter of face of inflorescence up to 5½ inches at maturity; golden yellow ray floret color devoid of bronze tinging and with minimal color oxidation; flowering response which is uniform and consistent, resulting in a flowered plant approximately 8 weeks from the beginning of short day treatment; growth habit which is strong and semi-spreading; tall height which is responsive to daylength and B–9 for adaptability to various pot sizes; foliage which is dark green and glossy; durability of the flowered plant which ranges up to 21 days at average home temperatures of 68° F. to 75° F., and peduncles which became brittle and weak during low light periods of the year (November thru April).

No references cited.

ROBERT E. BAGWILL, Primary Examiner